United States Patent [19]

Saltman et al.

[11] Patent Number: 5,232,709
[45] Date of Patent: Aug. 3, 1993

[54] CALCIUM AND TRACE MINERAL SUPPLEMENTS COMPRISING ESTROGEN

[75] Inventors: Paul D. Saltman, La Jolla, Calif.; Kenneth T. Smith, Cincinnati, Ohio

[73] Assignee: The Procter & Gamble Company, Cincinnati, Ohio

[21] Appl. No.: 882,199

[22] Filed: May 13, 1992

Related U.S. Application Data

[62] Division of Ser. No. 562,773, Aug. 6, 1990, Pat. No. 5,151,274.

[51] Int. Cl.$^5$ .................. A61K 31/565; A61K 33/06; A61K 33/30; A61K 33/34
[52] U.S. Cl. .................................. 424/630; 424/639; 424/641; 424/682; 514/182
[58] Field of Search ............... 424/630, 639, 641, 682; 514/182, 574

[56] References Cited

U.S. PATENT DOCUMENTS

| | | | |
|---|---|---|---|
| 3,949,098 | 4/1976 | Bangert | 426/324 |
| 3,950,547 | 4/1976 | Lamar, III et al. | 426/74 |
| 3,992,555 | 11/1976 | Kovacs | 426/72 |
| 4,070,488 | 1/1978 | Davis | 426/72 |
| 4,107,346 | 8/1978 | Kronitz | 426/648 |
| 4,214,996 | 7/1980 | Buddemeyer et al. | 252/1 |
| 4,351,735 | 9/1982 | Buddemeyer et al. | 252/1 |
| 4,419,369 | 12/1983 | Nichols et al. | 426/2 |
| 4,497,800 | 2/1985 | Larson et al. | 514/2 |
| 4,722,847 | 2/1988 | Heckert | 426/74 |
| 4,786,510 | 11/1988 | Nakel et al. | 424/648 |
| 5,128,374 | 7/1992 | Kochanowski | 514/574 |
| 5,186,965 | 2/1993 | Fox et al. | 426/74 |

FOREIGN PATENT DOCUMENTS 2845570 4/1980 Fed. Rep. of Germany.
56-097248 12/1979 Japan.

OTHER PUBLICATIONS

Hughes et al., "Effects of Calcium Carbonate and Hydroxyapatite on Zinc and Iron Retention in Postmenopausal Women, American Journal of Clinical Nutrition", Jul. 1986, pp. 83–88.
S. V. Ting, "Nutrients and Nutrition of Citrus Fruits", ACS, 1980, Hungerford, et al., "Interactions of pH and Ascorbate in Intestinal Iron Absorption" American Institute of Nutrition, 1983, pp. 2615–2622.
Riis et al., "Does Calcium Supplementation Prevent Postmenopausal Bone Loss?", New England J. of Medicine, 316, pp. 173–177 (1987).
L. Nilas et al., "Calcium Supplementation and Postmenopausal Bone Loss", British Medical Journal, 289, pp. 1103–1106 (1984).
H. Spencer et al., "NIH Concensus Conference: Osteoporosis", Journal of Nutrition, 116, pp. 316–319 (1986).
W. A. Peck, et al., Physician's Resource Manual on Osteoporosis National Osteoporatic Foundation (1987).
Reginster, et al., "Trace Elements and Postmenopausal Osteoporosis: A Preliminary Study of Decreased Serum Manganese", Med. Sci. Res., 16, pp. 337–338 (1988).
Strause, et al. "The Effect of Deficiencies of Manganese and Copper on Osteoinduction and on Resorption of Bone Particles in Rats", Calcif. Tissue Int. 41, pp. 145–150 (1987).
R. C. Haynes, Jr., et al. "Agents Affecting Calcification", Pharmacological Basis of Therapeutics, (1985), 7th Ed. pp. 1517–1543.
G. D. Whedon et al., "An Analysis of Current Concepts and Research Interests in Osteoporosis", Current Advances in Skeletogenesis, (1985), pp. 327–333.

(List continued on next page.)

Primary Examiner—Allen J. Robinson
Assistant Examiner—S. Mark Clardy
Attorney, Agent, or Firm—Rose Ann Dabek; Jerry J. Yetter

[57] ABSTRACT

Nutritional mineral supplements comprising calcium citrate malate and salts of manganese, copper and zinc are disclosed. These supplements, which provide at least 25% RDA of the minerals, are used in addition to the normal diet. These supplements are useful for increasing bone growth and for treating age-related bone loss in humans and animals.

9 Claims, No Drawings

OTHER PUBLICATIONS

Smith, K. T. et al., Calcium absorption from a new calcium delivery system (CCM) Calcif. Tissue Int. 1987; 41:351-2.

Miller, J. Z. et al., Calcium absorption from calcium carbonate and a new form of calcium (CCM) in healthy male and female adolescents. Am. J. Clin. Nutr. 1988: 48:1291-4.

Miller, J. Z. et al., Calcium absorption in children estimated from single and double stable calcium isotope techniques, Dlinica Chemical Acta 1989; 183:107-14.

Dawson-Hughes, B. et al. A controlled trial of the effect of calcium supplementation on bone density in postmenopausal women, N. Engl. J. Med. 1990:323-87-8-83.

Kochanowski, B. A., Effect of calcium citrate-malate on skeletal development in young, growing rats. J. Nutr., 1990: 120:876-81.

Kanerva, R. L. et al., Bioavailability of calcium from supplemental and food fortification sources, FASEB J. 1989: 3:A771.

Kanerva, R. L. et al. Assessing human bioavailability potential of calcium sources using a rat model, J. Bone Min. Res. 1990: 5:S176.

Sheikh, M. S. et al., Gastrointestinal absorption of calcium from milk and calcium salts, N. Engl. J. Med. 1987: 217: 532-6.

Sheikh, M. S. et al., Reduction of dietary phosphorus absorption by phosphorus binders: a theoretical, in vitro, an in vivo study, J. Clin. Invest. 1989; 83:66-73.

Garcia-Lopez, S. et al. Bioavailability of calcium from four different sources, Nutr. Res. 1991: 11:1187-96.

Recker, R. R. Calcium absorption and achlorhydria, N. Eng. J. Med. 1985: 313:70-3.

Bo-Linn, G. W. et al., An evaluation of the importance of gastric acid secretion in the absorption of dietary calcium. J. Clin. Invest. 1984: 73:7640-47.

Yano, K. et al. The relationship between diet and bone mineral content of multiple skeletal sites in elderly Japanese-American men and women living in Hawaii, Am. J. Clin. Nutr. 1985: 42:877-88 (1985).

Holbrook, T. L. et al. Dietary calcium and risk of hip fracture: 14-year prospective population study, Lancet 1988: 2:1046-9.

CALCIUM AND TRACE MINERAL SUPPLEMENTS COMPRISING ESTROGEN

This is a division of application Ser. No. 07/562,773, filed on Aug. 6, 1990 U.S. Pat. No. 5,151,274.

TECHNICAL FIELD

The present invention relates to nutritional improvements in calcium supplements containing trace minerals, in particular copper, manganese and zinc. These supplements are useful for increasing bone growth and treating age-related bone loss. They can be used in conjunction with foods and beverages or taken as an oral solid or liquid supplement. The invention also relates to a method of building bone or treating bone loss in osteoporosis patients and post-menopausal women.

BACKGROUND OF THE INVENTION

Vitamin and mineral supplements for human and veterinary use are commonplace. Some diets, heavy physical exercise and disease conditions may require the intake of considerable quantities of minerals apart from those generally obtained through what otherwise would be considered a normal diet. Calcium and trace mineral supplementation is important primarily for those who have inadequate diets, including growing children. Older adults have an additional need for calcium to help prevent the bone loss which occurs as a normal consequence of the aging process. In particular, postmenopausal women need additional calcium due to hormonal changes which can accelerate the bone loss rate leading to a further diminishment in bone mass.

The trace minerals which affect bone growth are copper, zinc and manganese. Supplementation of the diet with these minerals along with a highly bioavailable source of calcium is highly desirable. Commercially available mineral supplements are useful in many circumstances where increased mineral intake is desirable. Most of these multi-vitamin and multi-mineral tablets are low in calcium, requiring separate supplementation with calcium sources. In addition, not all calcium sources are equal in terms of bioavailability and absorption. It would be more convenient if all of the minerals could be administered conjointly in a convenient and/or pleasant tasting form which would not require extra attention, planning and implementation by the user. This could be done in the form of foods and beverages as well as in the form of tablets.

There are well-recognized problems associated with adding both mineral and calcium supplements to foods and beverages. Some of these are taste; calcium tends to be chalky in flavor. In addition, the solubility of many calcium sources prevents them from being added to many beverages. Others are interactions of the minerals with the food or beverage which affects the stability and/or the bioavailabilty of the product. This invention provides a means for making such product.

This invention also relates to methods of building bone in humans and other animals, i.e., for the treatment of age-related bone loss and related disorders. In particular, this invention relates to such methods of treatment by administration of certain calcium salts and the minerals, copper, zinc and manganese.

Calcium is the fifth most abundant element in the human body. It plays an important role in many physiological processes, including nerve and muscle functions. Not surprisingly, nutritional and metabolic deficiencies of calcium can have broad-ranging adverse effects. Since about 98% to 99% of the body's calcium is found in bone tissues, many of these adverse effects are manifested through deficiencies in the structure, function and integrity of the skeletal system.

The most common metabolic bone disorder is osteoporosis. Osteoporosis can be generally defined as the reduction in the quantity of bone, either from the reduction in bone formation or the acceleration of bone resorption, in either event the result is a decrease in the amount of skeletal tissue. In general, there are two types of osteoporosis: primary and secondary. "Secondary osteoporosis" is the result of an identifiable disease process or agent. However, approximately 90% of all osteoporosis cases are idiopathic "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the wrist, hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. Two reactions are involved, bone loss or resorption and bone growth or accretion. This remodeling occurs in a series of discrete pockets of activity in the bone, called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

In young healthy adults, the rate at which the osteoclasts and osteoblasts are formed maintains a balance of bone resorption and bone formation. However, as normal consequency of aging an imbalance in this remodeling process develops, resulting in loss of bone at a rate faster than the accretion of bone. As imbalance continues over time the reduction in bone mass and thus bone strength leads to fractures.

Many compositions and methods are described in the medical literature for the "treatment" of osteoporosis. See, for example, R. C. Haynes, Jr. et al., "Agents affecting Calcification", *The Pharmacological Basis of Therapeutics*, 7th Edition (A. G. Gilman, L. S. Goodman et al., Editors, 1985); and G. D. Whedon et al., "An Analysis of Current Concepts and Research Interest in Osteoporosis", *Current Advances in Skeletogenesis* (A. Ornoy et al., Editors, 1985). Estrogen is often used to affect the metabolism of calcium by influencing the osteoblast cells. Treatments using fluoride have also been described. However, the utility of such agents may be limited, because of possible adverse side effects. See W. A. Peck, et al., *Physician's Resource Manual on Osteoporosis* (1987), published by the National Osteoporosis Foundation.

Nutritional therapies for osteoporosis have also been proposed. Many calcium-containing compounds and compositions have been described for use as nutritional supplements. Many commercial preparations are also available, typically containing calcium carbonate or calcium phosphate. Other calcium salts have also been described for use in calcium supplements, including calcium lactate, calcium citrate and calcium gluconate.

U.S. Pat. No. 3,949,098 issued Bangert (assigned Nabisco, 1976) describes a nutritious orange drink concentrate that contains whey protein. The patent suggests the addition of minor amounts of vitamins and other nutrients which include various cupric salts, manganese salts, zinc salts, as well as calcium salts.

German OLS 2,845,570 issued to E.R.E. (Europe Representation Establishment, 1980) describes a honey containing composition. Honey contains low levels of calcium, manganese, copper as well as trace amounts of magnesium, iron, phosphorous, silicon and nickel. The value of honey as a medicant is undisputed according to this patent application. This application claims a honey containing composition with levarotatory ascorbic acid and citric acid. This patent has issued as U.S. Pat. No. 4,243,794 (1981).

U.S. Pat. No. 4,497,800 issued to Larsen et al (assigned Mead Johnson & Company, 1985) describes a nutritionally complete ready-to-use liquid diet for providing total patient nourishment. The diet contains free amino acids and small peptides, a carbohydrate source, and nutritionally significant amounts of all essential vitamins and minerals, and stabilizers. The minerals include calcium, copper, zinc and manganese, among others. Most of these minerals are given as the gluconate salt.

"Effects of calcium carbonate in hydroxyapatite on zinc and iron retention in postmenopausal women", Dawson-Hughes, Seligson and Hughes, *American Journal of Clinical Nutrition*, 44, 83–88 (1986) describes the effect of calcium carbonate on whole-body retention of zinc and iron in thirteen healthy post menopausal women. The test meal, including both dry food and a formulated beverage, included calcium, copper and zinc at a level of one-third the usual daily requirement. These are levels normally found in human diets.

U.S. Pat. No. 3,992,555 issued to Kovacs (assigned Vitamins, Inc., 1976) describes food supplements prepared by mixing assimilable iron compounds, vitamins and minerals with a heated edible fat carrier. The minerals include calcium, zinc, copper, and manganese among others.

U.S. Pat. No. 3,950,547 issued to Lamar et al (assigned Syntex Inc, 1976) describes a dietary composition containing peptides and/or amino acids, lipids and carbohydrates in an aqueous emulsion. Suitable minerals for adding at low levels include among others calcium, copper and zinc.

U.S. Pat. No. 4,107,346 issued to Kravitz (1978) describes a dietary salt composition for use as a replacement for salt in foods. The role of copper is described as a component of several enzymes essential for nutrition. The patent further discloses that "spontaneous fractures are common in animals feeding off copper deficient soils or who are given artificially depleted copper diets". (column 4, lines 20-30) Zinc is described as helping in growth, wound healing and improving taste and smell. Clinical symptoms of manganese deficiency have not been observed in man. However, there is no question that manganese is essential for human nutrition. Main manifestations of its deficiency are impaired growth and skeletal abnormalities. Calcium is described as being necessary for blood coagulation, for calcium retention, and for relieving the symptoms of osteoporosis. Examples of salts that contain these four trace minerals are disclosed.

U.S. Pat. No. 4,070,488 issued to Davis (unassigned, 1978) discloses a highly stabilized balanced nutritive composition useful in supplementing the diet of humans and/or animals. This composition contains gelatin. The patent discloses that the sulfhydryl groups of the gelatin can render copper inactive toward ascorbic acid.

U.S. Pat. No. 4,214,996 issued to Buddemeyer et al (R.G.B. Laboratories, 1980) discloses mineral compositions which are very soluble. These compositions contain calcium, phosphorus, zinc, as well as manganese. Not all of the compositions that are described contain all four elements.

U.S. Pat. No. 4,351,735 to Buddemeyer et al (R.G.B. Laboratories, 1982) is related to the '996 patent.

"Nutrients and Nutrition of Citrus Fruits," *Citrus Nutrition and Quality*, Ting, (American Chemical Society, 1980) discloses the presence of certain trace minerals in orange juice. These include copper, zinc, iron and manganese. Calcium and magnesium are the two major divalent cations in orange juice. The levels of all the minerals are low.

Hungerford et al, "Interaction of pH and ascorbate in intestinal iron absorption," (1983) describes the iron absorption from various food materials. The diet which was low in iron also contained calcium carbonate, manganese sulfate and copper sulfate among others.

U.S. Pat. No. 4,419,369 issued to Nichols et al (assigned Baylor College of Medicine, 1983) describes an improved dietary protein mineral module for infants. An approximate analysis of the material shows the presence of iron, zinc, copper and calcium.

The utility of these known supplements varies. Unlike agents (such as estrogen) which affect the metabolism of bone, calcium nutritional supplements have been thought to merely provide a source for calcium (which may or may not be properly absorbed and metabolized). See, for example, B. Riis et al., "Does Calcium Supplementation Prevent Postmenopausal Bone Loss?," *New England J. of Medicine*, 316, 173–177 (1987); L. Nilas et al., "Calcium Supplementation and Postmenopausal Bone Loss," *British Medical Journal*, 289, 1103–1106 (1984); and H. Spencer et al., "NIH Concensus Conference: Osteoporosis," *Journal of Nutrition*, 116, 316–319 (1986).

It has now been discovered, however, that the administration of mixtures of certain calcium salts, along with trace minerals, copper, zinc and manganese are surprisingly effective for delaying age-related loss of bone. In particular, as compared to nutritional regimens known in the art, these methods afford greater efficacy in the treatment of age-related bone loss and related disorders.

It would be desirable, therefore, to have mixed calcium and mineral supplements which are compatible and nutritionally available. It would also be quite useful to have such supplements which could be added to food and beverage compositions without undesirably affecting organoleptic or aesthetic properties.

It is an object of the present invention to provide calcium mineral supplements which provide bone growth and can be used to treat age-related bone loss or to correct the imbalance that occurs between bone formation and bone resorption.

It is a further object of this invention to provide foodstuffs, beverages and beverage concentrates which are supplemented with calcium and trace minerals.

These and other objects are secured herein, as will be seen from the following disclosure.

SUMMARY OF THE INVENTION

The multimineral supplements employ specific calcium salts of mixtures of citric and malic acids. The copper, manganese and zinc salts are salts of sulfate, nitrate and chloride and carboxylates, e.g. gluconates.

The present invention provides methods for building bone in a human or other animal subject, comprising administering to said subject a safe and effective amount of calcium citrate malate and of copper, zinc and manganese salts. The calcium citrate malate comprises a complex or a mixture of calcium salts having a ratio of moles citrate to moles malate of from about 1:0.16 to about 1:13.5. The calcium citrate malate is preferably administered in an oral dosage form, containing pharmaceutically-acceptable carriers and excipients.

All ratios, proportions and percentages herein are by weight, unless otherwise specified. All weights of the minerals are on an elemental basis unless otherwise specified.

DETAILED DESCRIPTION OF THE INVENTION

The present invention relates to stable mineral supplements and supplemented foods and beverages including dry beverage mixes and to a method of building bone.

As used herein, the term "comprising" means various components can be conjointly employed in the mineral supplements, foods and beverages of the present invention. Accordingly, the terms "consisting essentially of" and "consisting of" are embodied in the term comprising.

By "nutritional" or "nutritionally-supplemental amount" herein is meant that the mineral sources used in the practice of this invention provide a nourishing amount of said minerals. This supplemental amount will comprise at least 25% of the Recommended Dietary Allowance (RDA) of the daily intake of calcium, copper, manganese and zinc. Preferably, at least 50% of the Recommended Dietary Allowance (RDA) will be provided. The RDA for minerals is as defined in The United States of America (see Recommended Daily Dietary Allowance-Food and Nutrition Board, National Academy of Sciences-National Research Council). This is supplemental or in addition to the amount found in the diet.

As used herein, the term "flavors" includes both fruit and botanical flavors.

As used herein the term "sweeteners" includes sugars, for example, glucose, sucrose, and fructose. Sugars also include high fructose corn syrup solids, invert sugar, sugar alcohols, including sorbitol, and mixtures thereof. Artificial sweeteners are also included in the term sweetener.

As used herein, the term "trace minerals" means copper, manganese and zinc. These minerals play an important role in nutrition, but are required in only small or trace amounts in the diet. All three of these minerals are important enzymatic cofactors which are essential in development of bone in animals and humans. The trace minerals herein are administered in the form of pharmaceutically acceptable salts.

The "carboxylate counterion" used in the preparation of the preferred mineral salts herein can be any ingestible carboxylate species. However, some judgement must be made with regard to flavor contribution. For example, citrate, malate and ascorbate yield ingestible complexes whose flavors are judged to be quite acceptable, particularly in fruit juice beverages. Tartaric acid is acceptable, particularly in grape juice beverages, as is lactic acid. Longer-chain fatty acids may be used in solid mineral supplements, but can affect flavor and water solubility. For essentially all purposes, the malate (preferred), gluconate, citrate and ascorbate moieties suffice, although others can be selected, according to the desires of the formulator.

The counterion for the trace minerals can also be phosphate, chloride, sulfate, nitrate or the like. However, such counterions can undesirably interact with calcium ions, especially in beverages. In high concentrations, these counterions, particularly chloride and sulfate, may contribute an undesirable flavor note. Accordingly, the carboxylate counterions noted above are preferred herein.

The methods of the present invention comprise the administration of calcium citrate malate to a human or other animal subject along with the trace mineral salts. Specific compounds and compositions to be used in these processes must, accordingly, be pharmaceutically acceptable. As used herein, a "pharmaceutically acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

Trace Mineral Component

In supplements of the type disclosed herein, the nutritionally supplemental amount for the minerals will generally comprise more than 50% of the RDA and preferably 80%-100% RDA, most preferably 100% of the RDA, per unit portion of the finished supplement. Of course, it is recognized that the preferred daily intake of any mineral may vary with the user.

In general, the RDA (calcium) will range from 360 mg per 6 Kg for infants to 800 mg/54–58 Kg female, depending somewhat on age. Moreover, it can be difficult to supplement beverages with more than 20–30% RDA of calcium (based per serving) without encountering precipitation and/or organoleptic problems. However, this level of supplementation is equivalent to cow's milk in calcium value, and is therefore acceptable.

The estimated safe and adequate daily intake for zinc is 15 milligrams (mg) per day for males and 12 mg per day for females. There is no specific RDA for manganese and copper. A safe and adequate range has been established as 2 to 5 mg for manganese and for copper, the range is 1.5 mg to 3 mg per day.

Any soluble salt of the trace minerals can be used, for example, zinc chloride, zinc sulfate, manganese sulfate, manganese gluconate, copper sulfate and copper gluconate are useful. A nutritionally supplemental amount of these minerals is used. However, the particular salt used and the level will depend upon their interaction with other supplement ingredients.

Inorganic anions which are useful for making the trace mineral salts are sulfate, nitrate, phosphate, hydrogen phosphate and carbonate.

It is essential to this supplementation that the calcium salts be soluble in the stomach. This solubilization aids in making the calcium more readily bioavailable. It is equally important that the trace minerals be solubilized and absorbed by the stomach and or intestine. Therefore the choice of calcium and mineral salts depends upon the interaction of the salts in acid (stomach pH) solutions or basic (intestinal pH) solutions.

Solubility also plays an important role in the preparation of foods and beverages containing these supplements.

Calcium Citrate Malate Compositions:

The methods of this invention involve administration of a mixture of calcium salts, herein "calcium citrate malate," comprising calcium salts of citric acid and malic acid. The calcium citrate malate may consist of a mixture of calcium citrate and calcium malate, a complex of calcium containing citrate and malate ligands, a mixture of a calcium salt with citric acid and malic acid, or combinations thereof. (Mixtures of a calcium salt and citric and malic acids may be used to form calcium citrate malate in situ, in a liquid dose form, or in the acid environment of the stomach of the subject to whom the mixture is administered.) Preferred are calcium citrate malate mixtures made by adding calcium carbonate, calcium hydroxide or other suitable source to a mixture of citric and malic acid.

The molar ratio of citrate:malate is from about 1:0.16 to about 1:13.5, preferably from about 1:0.5 to about 1:4.5, more preferably from about 1:0.75 to about 1:3. The ratio of moles calcium:total moles citrate:total moles of malate is from about 2:1:1 to about 6:3:4, preferably from about 4:2:3 to about 6:3:4. The calcium citrate malate may contain other acid anions in addition to citrate and malate. Such anions may include, for example, carbonate, hydroxide, and mixtures thereof depending on the calcium source.

Preferably, the calcium citrate malate is neutral, comprised entirely of citrate and malate anions. Thus, preferably, the equivalents of calcium (2×moles calcium) is about equal to the total number of equivalents of citrate (3×moles citrate) plus malate (2×moles malate). A preferred calcium citrate malate has a calcium:citrate:-malate molar composision of about 6:2:3.

The calcium citrate malate and trace mineral salts for use in the methods of this invention may be provided in solid or liquid dosage forms. Calcium citrate malate for use in solid forms may be made, for example, by first dissolving citric acid and malic acid, in the desired molar ratio, in water. Calcium carbonate may then be added to the solution, in such amount that the ratio of moles calcium to moles citrate and moles malate is as desired. Carbon dioxide will be evolved. The solution may then be dried (as by freeze drying or oven drying at temperatures below 100° C.) to obtain the calcium citrate malate. Methods for making calcium citrate malate are described in the following documents: Co-pending application of Fox et al, Ser. No. 07/537313 filed Jun. 14, 1990; Japanese Patent Specification SHO 56-97248, Kawai, published Aug. 5, 1981; and in U.S. Pat. No. 4,722,847 issued to Heckert (1988).

Flavor Component

The flavor component of the present invention contains flavors selected from natural flavors, botanical flavors and mixtures thereof. The term "fruit flavors" refers to those flavors derived from the edible reproductive part of a seed plant, especially one having a sweet pulp associated with the seed. Also included within the term "fruit flavor" are synthetically prepared flavors made to simulate fruit flavors derived from natural sources.

The term "botanical flavor" refers to flavors derived from parts of a plant other than the fruit; i.e. derived from bean, nuts, bark, roots and leaves. Also included within the term "botanical flavor" are synthetically prepared flavors made to simulate botanical flavors derived from natural sources. Examples of such flavors include cocoa, chocolate, vanilla, coffee, kola, tea, and the like. Botanical flavors can be derived from natural sources such as essential oils and extracts, or can be synthetically prepared.

The particular amount of the flavor component effective for imparting flavor characteristics to the supplements and food or beverage mixes of the present invention ("flavor enhancing") can depend upon the flavor(s) selected, the flavor impression desired, and the form of the flavor component. The flavor component can comprise at least 0.05% by weight of the beverage composition and preferably from 0.05% to about 10%. The amount of flavor added to the food, beverage or supplement is within the skill of one in the art and depends on the flavor intensity desired.

For chocolate or cocoa, the amount of flavor added is from about 0.05% to about 20%. Lower levels of artificial or synthetic chocolate flavors are used than for cocoa itself.

The beverages can be flavored with fruit or other botanical flavors, e g., vanilla, strawberry, cherry, pineapple, banana, and mixtures thereof.

Sweetener Component

The sweetener composition is usually a monosaccharide or a disaccharide. These include sucrose, fructose, dextrose, maltose and lactose. Other carbohydrates can be used if less sweetness is desired. Mixtures of these sugars can be used.

In addition to sugar of the present invention can contain other natural or artificial sweeteners. Other suitable sweeteners include saccharin, cyclamates, acetosulfam, L-aspartyl-L-phenylalanine lower alkyl ester sweeteners (e.g. aspartame), L-aspartyl-D-alanine amides disclosed in U.S. Pat. No. 4,411,925 to Brennan et al., issued Oct. 23, 1983, L-aspartyl-D-serine amides disclosed in U.S. Pat. No. 4,399,163 at Brennan et al., issued Aug. 16, 1983, L-aspartyl-L-1-hydroxymethylalkaneamide sweeteners disclosed in U.S. Pat. No. 4,338,346 to Brand, issued Dec. 21, 1982, L-aspartyl-1-hydroxyethylalkaneamide sweeteners disclosed in U.S. Pat. No. 4,423,029 to Rizzi, issued Dec. 27, 1983, L-aspartyl-D-phenylglycine ester and amide sweeteners disclosed in European Patent Application 168,112 to J. M. Janusz, published Jan. 15, 1986, and the like. A particularly preferred sweetener is aspartame.

The amount of the sweetener effective in the food, beverage, mixes or supplements of the invention depends upon the particular sweetener used and the sweetness intensity desired. For noncaloric sweeteners, this amount varies depending upon the sweetness intensity of the particular sweetener. For sugar (i.e., sucrose), this amount can be from 10% to 85% (typically from 55% to 70%) by weight. In determining the amount of sugar, any sugar or other sweetener present in the flavor component is also included. Low-calorie sweetener combinations containing a noncaloric sweetener such as aspartame and a sugar, such as corn syrup solids, or sugar alcohols can also be used in beverage mixes. In general, the amount of sweetener will be from about 0.5% to about 85%.

Other Ingredients

Other minor ingredients are frequently included in supplements, foods and beverages. Such ingredients include preservatives such as benzoic acid and salts thereof, sulfur dioxide, butylated hydroxyanisole, butylated hydroxytoluene, etc. Also, typically included are colors derived either from natural sources or synthetically prepared.

Salt, e.g. sodium chloride, and other flavor enhancers can be used to improve the flavor of the food, beverage or supplement.

Emulsifiers can also be included. Any food grade emulsifier can be used. Lecithin is a preferred emulsifier. Other edible emulsifiers include mono- and diglycerides of long chain fatty acids, preferably saturated fatty acids, and most preferably, stearic and palmitic acid mono- and diglycerides. Propylene glycol esters are also useful in beverage mixes.

Fats or oils can also be added to supplements or foods to make them more palatable.

Supplement Forms

Solid forms include tablets, capsules, granules and bulk powders. Tablets may contain suitable binders, lubricants, diluents, disintegrating agents, coloring agents, flavoring agents, flow-inducing agents and melting agents. Liquid oral dosage forms include aqueous solutions, emulsions, suspensions, solutions and/or suspensions reconstituted from non-effervescent granules and effervescent preparations reconstituted from effervescent granules. Such liquid oral dosage forms may contain, for example, suitable solvents, preservatives, emulsifying agents, suspending agents, diluents, sweeteners, melting agents, and coloring and flavoring agents. A preferred liquid dosage form contains calcium citrate malate and the trace minerals in a juice-containing beverage or other beverage.

The trace minerals and calcium citrate malate can be coadministered in one tablet, liquid, food or beverage or they can be administered separately. A capsule containing the trace mineral salts and a second tablet with the calcium citrate malate are easy to formulate and to swallow. A mineral supplement could also be coadministered with a calcium beverage.

Specific examples of pharmaceutically acceptable carriers and excipients that may be used to formulate oral dosage forms of the present invention are described in U.S. Pat. No. 3,903,297, Robert, issued Sep. 2, 1975. Techniques and compositions for making dosage forms useful in the methods of this invention are described in the following references; 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition. (1976).

Method of Building Bone

Various oral dosage forms of calcium citrate malate and trace minerals may be used in the present invention. Such dosage forms comprise a safe and effective amount of calcium citrate malate, trace minerals and a pharmaceutically acceptable carrier. Preferably the pharmaceutically acceptable carrier is present at a level of from about 0.1% to about 99%, preferably from about 0.1% to about 75%, by weight of the composition. Unit dosage forms (i.e., dosage forms containing an amount of calcium citrate malate suitable for administration in one single dose, according to sound medical practice) preferably contain from about 100 mg to about 1000 mg, preferably from about 100 mg to about 500 mg, more preferably from about 200 mg to about 300 mg of calcium (on an elemental basis). Unit dosage forms of copper (on an elemental basis) contain 0.5 to 5 mg, preferably 0.5 to 4.0 mg, of manganese (on an elemental basis) contain 1 to 8 mg and preferably from 2 mg to 7 mg, and of zinc (on an elemental basis) contain 1.5 to 30 mg and preferably 7.5 to 20 mg zinc.

Specifically, the present invention provides a method for building bone in a human or other animal subject, comprising administering to said subject a safe and effective amount of calcium citrate malate, and copper, zinc and manganese for a period of time sufficient to achieve an increase in the net skeletal mass of said subject. As used herein, "building bone" refers to a decrease in the net skeletal loss of bone of the subject treated and therefore a net skeletal increase in mass. The slowing of the rate of bone loss and the increase in growth rate occur simultaneously so the net bone density may stay the same. The increase in mass may be at any skeletal site, including spine, hip, long bones of arms or legs. Preferably, the net skeletal mass is increased by at least about 0.1%, more preferably at least about 1%.

The loss of bone is cumulative over a long period of time. Typically, lifetime loss in bone mass is about 35% in males and 50% in females. Thus, even though a net skeletal increase of as little as 0.5% in one year is not particularly critical, over 10 years this results in 5% more bone mass than would be present if bone loss continued at its usual rate.

"Administering" refers to any method which, in sound medical practice, delivers the calcium citrate malate and trace minerals used in this invention to the subject to be treated in such a manner so as to be effective in the building of bone. Preferably, the calcium citrate malate is administered orally in 2 doses a day and the mineral supplements are orally administered in one dose a day. The calcium citrate malate and minerals could be mixed and administered in 2 or 3 doses a day if desired.

Preferably, from about 175 milligrams to about 2000 milligrams of calcium (as elemental calcium) are administered to said subject, per day. More preferably, from about 250 milligrams to about 1500 milligrams, most preferably from about 500 milligrams to about 1000 milligrams, of calcium are administered, per day. The specific amount of calcium citrate malate to be administered depends upon the relative percentage weight of calcium in the particular calcium citrate malate employed. From 0.5 to 5.0 mg of copper, 1.5 to 30 mg of zinc and 1 to 8 mg of manganese are administered. The preferred daily dose total is 1.0 to 3.0 mg copper, 7.5 to 20 mg zinc and 2 to 7 mg manganese. The weight is for the metal ion and not for the salt. By way of example, 19.9 mg of manganese chloride tetrahydrate supplies 5.5 mg manganese on an elemental basis.

The specific period of time sufficient to achieve an increase in the net skeletal mass of the subject may depend on a variety of factors. Such factors include, for example, the specific mineral formulation employed, the amount of minerals administered, the age and sex of the subject, the specific disorder to be treated, concomitant therapies employed (if any), the general physical health of the subject (including the presence of other disorders), the extent of bone loss in the individual, and the nutritional habits of the individual. Although the administration of even small quantities of calcium citrate malate and minerals may build bone, the net increase in bone mass may not be detectable for short periods of administration.

For the treatment of age-related bone loss, the calcium citrate malate and minerals are administered for at least about six months, preferably for at least about twelve months. Of course, such administration may be continued indefinitely, according to sound medical practice.

The methods of this invention may be employed in the treatment of any of a variety of disorders in which the building of bone is desired. Thus, preferably, the human or other animal "subject" of the methods of this invention is "in need" of a method for building bone, i.e., the subject has a disorder for which building of bone or decrease in rate of bone resorption would be advantageous according to sound medical practice. Such disorders include, for example, bone fractures, broken mass and disorders typified by bone loss, such as age-related bone loss and osteoporosis (both primary and secondary forms).

A preferred method of this invention is for the treatment of age-related bone loss. Such methods include administration of calcium citrate malate in combination with zinc, copper, manganese and other therapeutic agents. Estrogen therapy is commonly used. The method herein also comprises coadministering from about 0.6 mg to about 6 mg of estrogen along with the calcium and trace minerals. Preferably from 0.625 mg to about 1.25 mg of estrogen is taken daily. Any viable estrogen hormone replacement can be used.

The following example illustrates compositions of the type provided by the practice of this invention, but is not intended to be limiting thereof.

EXAMPLE I

Several post-menopausal women are treated by administering a composition containing calcium citrate malate having molar calcium:citrate:malate composition of about 6:2:3. The calcium citrate malate is made by first dissolving approximately 384.2 grams of citric acid and approximately 402.3 grams of malic acid in approximately 2 liters of water. This citrate/malate solution is then heated to approximately 55° C. (131° F.), with stirring. Separately, approximately 600.6 grams of calcium carbonate is added to approximately 1.2 liters of water, forming a slurry, with stirring.

The citrate/malate solution is then removed from its heat source, and the calcium carbonate slurry is added slowly, with stirring. The rate of addition is controlled, to contain the reaction as carbon dioxide is released. An additional quantity of water, approximately 0.4 liters, is finally added. The reaction mixture is then stirred for approximately 1 to 1.5 hours. The reaction is essentially complete as the pH of the solution equilibrates to approximately 4.3.

A precipitate of calcium citrate malate is thus formed. The excess reaction liquid is filtered off. The calcium citrate malate is dried, for approximately 12 hours at approximately 105° C. (221° F.), reducing the moisture level to less than about 1%. The dried product is then milled to approximately 10–20 mesh size, for a swallowable tablet formulation. Each tablet contains 250 mg.

The swallowable tablet dosage form is then made, comprising:

| Component | % (By Weight) |
|---|---|
| Calcium citrate malate* | 99.73 |
| Magnesium stearate | 0.27 |

*Having a molar calcium:citrate:malate composition of approximately 6:2:3, made as described above in this example.

The tablet formulation is made by thoroughly admixing the powders, and tabletting using a standard tablet press, to form tablets weighing approximately 1104 milligrams. The tablets are then coated, using a pan coater. The coating solution contains approximately 11% hydroxypropylmethyl cellulose, approximately 2% polyethylene glycol, approximately 3.5% colorant, and the balance of water.

A capsule containing 15 mg zinc (from zinc sulfate), 5 mg manganese (from manganese gluconate) and 2.5 mg copper (from copper gluconate) is also administered to each patient.

The density of the subject's lumbar vertebrae is determined by dual-energy x-ray absorptiometry. The human subject is then administered 4 of the calcium tablets and one trace mineral capsules comprised as above, each day for 12 months. The mass of the subject's vertebrae is then remeasured, indicating a net increase in bone mass. The following results are achieved after 1 year.

| | Change in Spine Bone Mineral Density | | |
|---|---|---|---|
| Treatments | Number Of Patients | % Change After 1 Year | Net Increase In Bone Mass |
| Calcium placebo/ Trace minerals placebo | 42 | −2.41 ± 0.63 | 0.00 |
| Calcium placebo/ trace minerals | 38 | −1.55 ± 0.66 | 0.86 |
| Calcium/trace minerals placebo | 34 | −1.28 ± 0.70 | 1.13 |
| Calcium and trace minerals | 37 | −0.17 ± 0.67 | 2.24 |

The table shows that the calcium and trace minerals supplement affects bone density and shows a net bone building effect of about 2.24% compared to the placebo group. The calcium trace mineral supplement effect is significantly different from the dual placebo treatment at a 95% confidence level. The dual placebo patients had at least a 2% loss over the one year period, the calcium/trace minerals patients showed little or no bone loss and thus a net increase of bone mass.

EXAMPLE II

Preparation of Calcium-Citrate-Malate

A calcium-citrate-malate solution is prepared by dissolving 2 parts sucrose and then 0.1 part citric and 0.28 part malic acids in 28.19 parts water. Calcium hydroxide (0.22 part) is added and the mixture is agitated. This solution can be used directly to prepare beverages, or can be freeze-dried to use in solid form.

EXAMPLE III

Preparation of Calcium-Citrate-Malate Without Sugar

In an alternate mode, the sucrose can be deleted from the above preparation. Thus, a calcium citrate-malate solution is prepared by admixing 62 g calcium carbonate with 11 g citric acid and 44 g malic acid dissolved in 1,040 g water at ambient temperature. This solution can be used to prepare low calorie beverages, beverage concentrates or freeze-dried for use in solid supplements. The calcium is 53% of the solid when dried to anhydrous conditions. Each ml of this solution provides 50 mg of calcium on an elemental basis.

EXAMPLE IV

A powdered mineral supplement comprising 2000 gm of calcium citrate malate prepared as above and 6.3 mg of copper sulfate (2.5 mg copper), 31.3 mg of zinc chloride (15 mg zinc) and 5 mg of manganese (15.4 mg of manganese sulfate monohydrate) is prepared by tabletting the mixture of powders.

EXAMPLE V

Mineral calcium-fortified chewable lozenges comprise:

| Ingredient | Amount |
| --- | --- |
| Calcium citrate-malate (6:2:3) | 2500 mg |
| Dextrose | 5 g |
| Fruit flavor* | 6 mg |
| Zinc Chloride | 31.3 mg |
| Manganese Gluconate | 12.5 mg |
| Copper Gluconate | 4.5 mg |
| Color | As desired |

*Fruit flavors used herein generally comprise synthetically reconstituted flavor esters. In this example, pineapple flavor is used and comprises a synthetic mixture of ethyl acetate, acetaldehyde, methyl n-valerate, methyl i-valerate, methyl i-caproate and methyl caprylate.

The lozenge of Example IV is prepared by mixing the ingredients and compacting the mixture in a standard press. This lozenge provides 936 mg calcium, 15 mg zinc, 1.5 mg manganese and 1.43 mg copper.

EXAMPLE VI

A chocolate powder mix is prepared as follows:

| Ingredient | Amount (percent) |
| --- | --- |
| Granular Sucrose | 66.88 |
| Non-fat Dry Milk | 15.00 |
| Sodium Chloride | 0.4 |
| Fermented Cocoa Powder, 14% fat | 16.0 |
| Lecithin | 1.0 |
| Colors | 0.07 |
| Butylated Hydroxytoluene (BHT) | 0.0003 |
| Ascorbic Acid | 0.21 |
| Zinc Chloride | 0.06 |
| Calcium Citrate Malate | 0.05 |
| Artificial Chocolate Flavor | 0.3 |

The lecithin is heated to 45° C. to melt it. The cocoa is sterilized at 160° C. in a pasteurizing oven for 2 hours.

A first premix is prepared by dry mixing the zinc salt and about one-half of the sodium chloride.

This premix is added to a dry mix of the remaining sodium chloride, vitamin C, and part of the non-fat dry milk. The colors and flavor are premixed with part of the non-fat dry milk solids (0.8% of final product). Cocoa powder, the remaining milk solids, minerals and the color/flavor mix are mixed together (22.88% of final product).

The BHT and lecithin are mixed together for one hour at 50° to 60° C. All of these mixes are then added to sucrose and blended to make a homogeneous dry mix.

This beverage is taken along with a capsule containing 1.5 mg of zinc as zinc chloride, 5 mg of manganese as manganese gluconate, 2.0 mg of copper as cupric gluconate.

What is claimed is:

1. A method for building of bone in a human subject suffering from age-related bone loss comprising administering to said subject a safe and effective amount of a mineral supplement comprising calcium citrate malate, zinc, manganese and copper salts for a sufficient period of time to build bones in said subject, said supplement being in a liquid dosage form.

2. A method for building of bone according to claim 1, wherein said dosage is a beverage.

3. A method according to claim 2 wherein said beverage contains juice.

4. A method according to claim 3 wherein said juice is selected from the group consisting of orange juice, apple juice, pear juice and cranberry juice.

5. A method according to claim 1 wherein said mineral supplement is added to dry beverage mixes.

6. A method for building of bone in a human subject suffering from age-related bone loss comprising administering to said subject a safe and effective amount of a mineral supplement comprising calcium citrate malate, zinc, manganese and copper salts for a sufficient period of time to build bone in said subject and wherein a safe and effective amount of estrogen is administered to the human subject.

7. A method according to claim 6 wherein said estrogen is administered in unit doses of from 0.6 mg to 6 mg.

8. A method according to claim 7 wherein said estrogen dose is from 0.6 mg to 1.2 mg.

9. A method of building bone according to claim 6, wherein said calcium citrate malate is administered at a level of from about 175 mg to about 2000 mg (on an elemental calcium basis), per day, said zinc is administered at a level of 1.5 to 30 mg/day, said manganese at a level of 1 to 8 mg/day and said copper is at a level of 1.0 to 5.0 mg/day.

* * * * *

UNITED STATES PATENT AND TRADEMARK OFFICE
CERTIFICATE OF CORRECTION

PATENT NO.  : 5,232,709
DATED       : August 3, 1993
INVENTOR(S) : P. D. Saltman
              K. T. Smith It is certified that error appears in the above-identified patent and that said Letters Patent is hereby corrected as shown below:

On the title page, item (73) Assignee:

Please add as an Assignee the Regents of the University of California.

Signed and Sealed this

Ninth Day of August, 1994

Attest:

BRUCE LEHMAN

Attesting Officer      Commissioner of Patents and Trademarks